United States Patent [19]

Smith

[11] Patent Number: 5,515,861
[45] Date of Patent: May 14, 1996

[54] TISSUE EXTRACTION TOOL

[76] Inventor: Jack V. Smith, 8505 42nd Ave., N., St. Petersburg, Fla. 33709

[21] Appl. No.: 381,548

[22] Filed: Jan. 31, 1995

[51] Int. Cl.$^6$ ................................................ A61B 10/00
[52] U.S. Cl. ........................................................ 128/754
[58] Field of Search ................................ 128/751–754; 606/167, 170, 184, 185

[56] References Cited

U.S. PATENT DOCUMENTS

| | | | |
|---|---|---|---|
| 2,623,521 | 12/1952 | Shaw | 128/754 |
| 2,919,692 | 1/1960 | Ackermann | 128/754 |
| 4,099,518 | 7/1978 | Baylis et al. | 128/754 |
| 4,142,517 | 3/1979 | Stavropoulos et al. | 128/754 |
| 4,177,797 | 12/1979 | Baylis et al. | 128/754 |
| 5,005,585 | 4/1991 | Mazza | 128/754 |
| 5,040,542 | 8/1991 | Gray | 128/754 |
| 5,271,414 | 12/1993 | Partika et al. | 128/754 |
| 5,318,040 | 6/1994 | Kensey et al. | 128/754 |

FOREIGN PATENT DOCUMENTS 2256369  12/1992  United Kingdom ............. 128/751

*Primary Examiner*—Max Hindenburg
*Attorney, Agent, or Firm*—Herbert W. Larson

[57] ABSTRACT

Tissue extraction tool includes a hollow cannula with a sharpened tip containing an aperture used to extract cylindrical core tissue samples of varying sizes from thin strips of tissue or paraffin embedded tissue. The tissue extraction tool contains a plunger with an optional spring for ejecting the cut tissue out of the sharpened tip of the device.

5 Claims, 2 Drawing Sheets

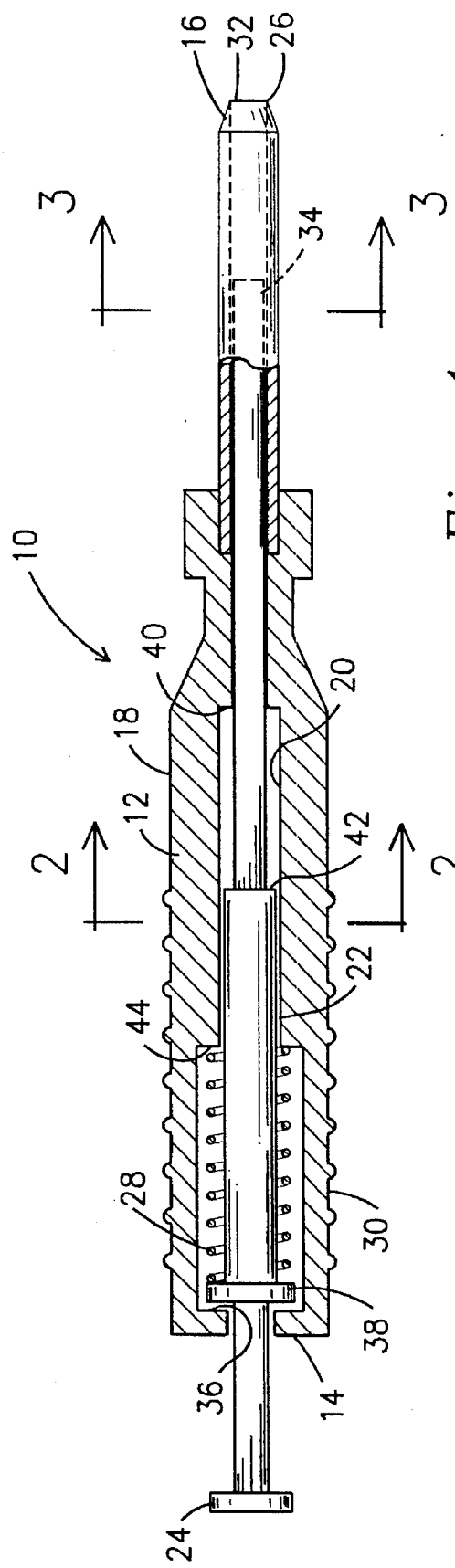

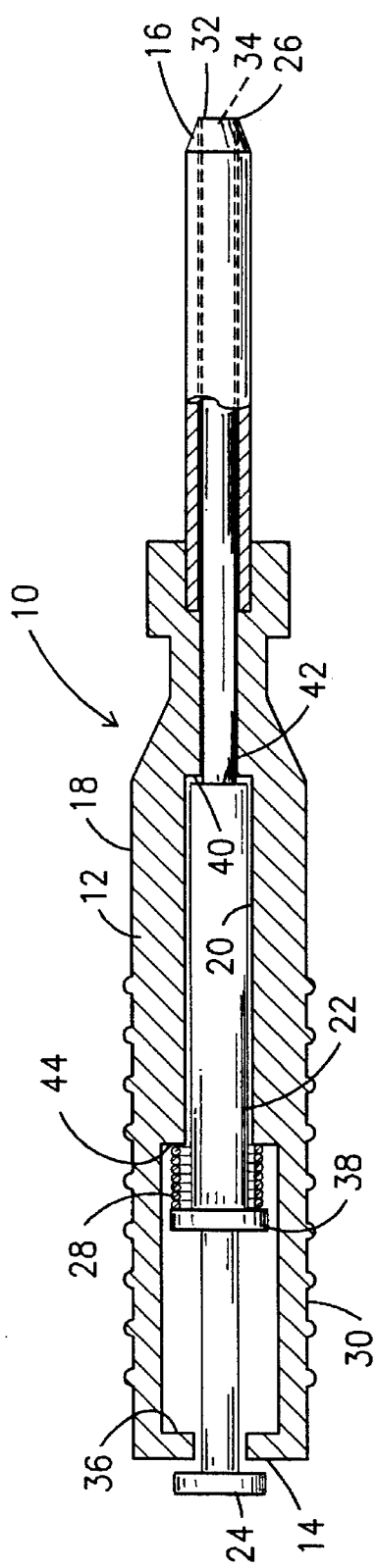
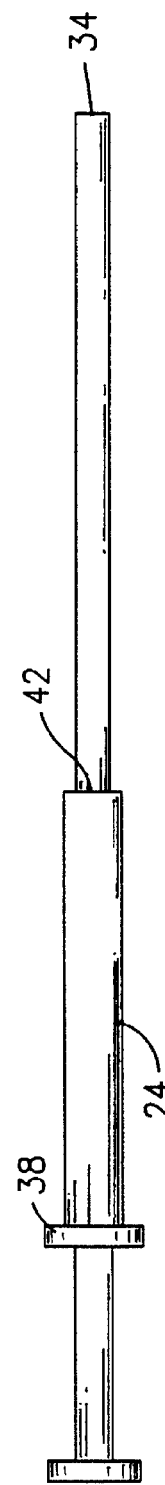
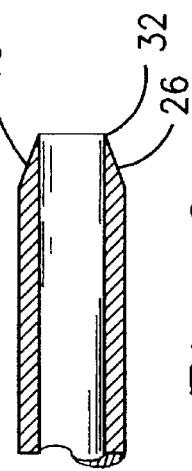
Fig. 4
Fig. 5
Fig. 6

TISSUE EXTRACTION TOOL

BACKGROUND OF THE INVENTION

This invention relates to a tissue extraction tool for use in extracting individual core tissue samples from selected tissues of interest for employment in various immunocytochemical techniques. This invention is particularly useful in taking core tissue samples from surgical pathology specimens imbedded in paraffin blocks. Also, This invention has the ability to cleanly cut core samples of varying sizes from 1 to 10 mm in diameter or even larger from a paraffin block. Such samples reduce the chance of false-negative immunocytochemical staining results caused by small sample sizes. The technique of preparing paraffin blocks as described by Battifora H: NOVEL METHOD FOR IMMUNOHISTOCHEMICAL ANTIBODY TESTING. *Lab Invest*, 55:244–248, 1986, results in a marked amount of false-negative immunocytochemical results because the sample size is too small. An improvement on Battifora is shown in Wan W. H., et al; A RAPID AND EFFICIENT METHOD FOR TESTING IMMUNOHISTOCHEMICAL REACTIVITY OF MONOCLONAL ANTIBODIES AGAINST MULTIPLE TISSUE SAMPLES SIMULTANEOUSLY. *J. Immunol Meth*, 103:121–129, 1987. However, this technique requires substantial effort and cost. A more simple technique is needed.

The rising cost of health care is a public concern because of its negative impact on the economy, general well being and health of the community at large. This twin issue of soaring costs and the deteriorating level of public health can be addressed by reducing cost at the laboratory workstation. The reduction of technician bench time by employing superior products and techniques, thus increasing quality, decreasing costs, and eliminating false-negative results, is becoming the primary concern of everyone in the health care field and the general public.

SUMMARY OF THE INVENTION

This invention is a single tissue extraction tool for extracting core tissue samples from paraffin embedded tissue and placing them into another paraffin block single-handedly. The tissue extraction tool of the invention has a hollow cannula with openings at each end, together with a distal end having a circular tapered aperture with a cutting edge. A solid plunger has an external diameter sufficient to be disposed in sliding contact with an inner surface of the hollow cannula. An optional spring around the plunger assists in ejecting the cut tissue out of the device.

The invention overcomes the problem of false-negative immunocytochemical results because larger sample sizes are obtained and this enables the technician to organize multiple tissue sampling in a paraffin block. The tissue extraction tool cuts the tissue sample cleanly in a circular disc shape, approximately 1 to 10 mm in diameter, depending on technician/pathologist preference. The tissue sample is removed from a paraffin bed by pulling the tool out of the paraffin bed. Then, the tissue extraction tool with the tissue core in a tip is placed in another paraffin bed by pressing a plunger. The plunger forces the tissue core out of the tip of the tool into the paraffin bed. The core samples can be placed in a rectangular grid-like fashion. When the multiple sample paraffin block is loaded, the technician can then stain the multiple sections (i.e., brain, lung, heart, etc.) with a variety of reagents. The tissue extraction tool enables the technicians/pathologist to perform multiple tissue staining simultaneously, instead of employing former laborious techniques.

BRIEF DESCRIPTION OF THE DRAWINGS

The features and benefits of the invention are best understood by those having ordinary skill in the art by reference to the following detailed description when considered in conjunction with the accompanying drawings as described below. The drawings are not necessarily to scale, emphasis instead being placed upon illustrating the principles of the invention. The tissue extraction tool is approximately 3 to 5 inches in length and approximately 8 to 10 mm in diameter. The size, shape, matrix, and weight can vary slightly depending upon manufacturing processes such as injection molding or machining, and materials employed, such as plastic, metals or composites.

FIG. 1 is a cross-sectional view of the tissue extraction tool of the present invention along its longitudinal axis.

FIG. 2 is a cross-sectional view along lines 2—2 of FIG. 1.

FIG. 3 is a cross-sectional view along lines 3—3 of FIG. 1.

FIG. 4 is a longitudinal cross-sectional view of the plunger depressed within the tool.

FIG. 5 is a longitudinal view of the plunger.

FIG. 6 is an enlarged cross-sectional view of tip cutting edge.

DETAILED DESCRIPTION OF THE PREFERRED EMBODIMENT

Throughout the following detailed description, the same reference numerals refer to the same elements in all figures.

The tool 10 shown in FIG. 1 has an outer hollow cannula 12 open at a first end 14 and second or distal end 16. The cannula 12 has an outer surface 18 and an inner surface 20, enclosing a channel 22.

As further shown in FIG. 1, a plunger 24 is cylindrical in shape and is used to force a cut tissue sample out of the tip 26 of the tool 10. An optional resilient means 28 encircles the plunger 24 and is used to force the plunger back up into the shaft 22 after the plunger 24 has forced the tissue sample out of the tip 26 of the tool 10. The resilient means 28 is preferably of metal, but other materials are suitable. A coil spring is the preferred resilient means.

The outer surface 18 of the cannula 12 adjacent first end 14 provides a gripping end 30 of the tissue extraction device 10, i.e. the end which is hand held. The cannula 12 and plunger 24 are preferably made of high impact plastic, but metal or other materials for the cannula 12 or plunger 24 may be substituted.

The tip 26 at the second end 16 of the cannula 12 is tapered and is cylindrical and hollow to hold the tissue core after sampling has taken place. The tip 26 housing is made of stainless steel or other metal. A sharpened circular edge 32 is the point of tissue contact for the tool 10. A blunt end 34 of plunger 24 is the point of tissue contact, both on obtaining the tissue and forcing the core sample out of the tip 26.

The inner wall 20 of cannula 12 has three ledges depending therefrom. The first ledge 36 is juxtaposed to a first flange 38 on the plunger 24 when the plunger is at rest. A second ledge 40 acts as a stop for flange 42 on plunger 24.

A third ledge 44 provides a stop for spring 28 so that plunger 24 returns to a resting position when spring 28 is no longer squeezed between flange 38 and ledge 44.

The tip 26 diameter at its widest point corresponds to a particular diameter of the cutting opening 32 as shown in the following table.

| TIP DIAMETER | DIAMETER OF CUTTING OPENING |
| --- | --- |
| 0.098 inches | 2 mm |
| 0.138 inches | 3 mm |
| 0.177 inches | 4 mm |
| 0.216 inches | 5 mm |
| 0.256 inches | 6 mm | with a tolerance of ±0.001 inches.

The plunger 24 is 3.972 inches in length with a diameter of 0.680 inches.

The cutting edge 32 should have a five degree angle and be sharply honed.

While the invention has been particularly shown and described with reference to a preferred embodiment thereof, it will be understood by those skilled in the art that various changes in form and details may be made therein without departing from the spirit and scope of the invention.

Having thus described the invention, what is claimed and secured by Letters Patent is:

1. A tissue extraction tool comprising an elongated cannula having openings at a first and second end, the first end having a means on an outer surface for gripping the cannula with one hand, the second end having an annular tapered aperture with a cutting edge, the cannula having an inner wall for slidably engaging a plunger, the cannula having a first and second ledge depending from the inner wall to prevent movement of the plunger beyond the first and second ledge, the plunger having a solid elongated body movable longitudinly within the inner wall of the cannula, a first and second end of the plunger having blunt surfaces, the plunger positioned in a retracted position with a first flange juxtaposed to the first ledge of the cannula when the cannula is inserted into tissue to cut the tissue and the plunger positioned in an extended position with a second flange juxtaposed to the second ledge of the cannula when the plunger is pushed by an external force to eject the cut tissue from the cannula.

2. The tissue extraction tool according to claim 1 further including a resilient means mounted on an outer surface of the plunger juxtaposed to the first flange and placed under tension between the first flange and a third ledge on an inner wall of the cannula when the plunger is pushed by the external force to eject the cut tissue.

3. The tissue extraction tool according to claim 2 wherein the resilient means is a coil spring.

4. The tissue extraction tool according to claim 1 wherein the cannula and plunger are made from high impact plastic.

5. The tissue extraction tool according to claim 4 wherein the second end of the cannula is made of stainless steel.

* * * * *